United States Patent
Numao et al.

(10) Patent No.: US 6,656,167 B2
(45) Date of Patent: Dec. 2, 2003

(54) PIERCING NEEDLE

(75) Inventors: Taku Numao, Osaka (JP); Masashi Ishida, Osaka (JP); Nobuo Wada, Osaka (JP); Takeshi Nizuka, Osaka (JP)

(73) Assignee: Nipro Corporation, Osaka (JP)

( * ) Notice: Subject to any disclaimer, the term of this patent is extended or adjusted under 35 U.S.C. 154(b) by 318 days.

(21) Appl. No.: 09/755,039

(22) Filed: Jan. 8, 2001

(65) Prior Publication Data
US 2001/0021832 A1 Sep. 13, 2001

(30) Foreign Application Priority Data
Jan. 7, 2000 (JP) .......................... 2000-001406

(51) Int. Cl.$^7$ ............................. A61M 25/00
(52) U.S. Cl. ...................... 604/272; 604/265
(58) Field of Search ................ 604/272, 265, 604/266; 29/527.2; 427/387, 388, 2, 409, 435, 452, 2.12, 2.28, 2.3

(56) References Cited

U.S. PATENT DOCUMENTS

| | | | | |
|---|---|---|---|---|
| 4,720,521 A | | 1/1988 | Spielvogel et al. ......... | 524/862 |
| 5,084,315 A | * | 1/1992 | Karimi et al. ............. | 428/36.6 |
| 5,266,359 A | * | 11/1993 | Spielvogel ............... | 427/388.4 |
| 5,536,527 A | * | 7/1996 | Prasad ...................... | 427/2.28 |
| 5,536,582 A | * | 7/1996 | Prasad et al. ............... | 427/387 |
| 5,736,251 A | | 4/1998 | Pinchuk ..................... | 428/447 |
| 5,911,711 A | * | 6/1999 | Pelkey ....................... | 604/265 |
| 6,015,398 A | | 1/2000 | Arimatsu et al. ........... | 604/272 |
| 6,106,473 A | * | 8/2000 | Violante et al. ............ | 600/458 |
| 6,117,480 A | * | 9/2000 | Spallek et al. .............. | 427/2.3 |

FOREIGN PATENT DOCUMENTS

| | | |
|---|---|---|
| EP | 0 878 206 A2 | 11/1998 |
| JP | 7-178759 A | 7/1995 |

* cited by examiner

Primary Examiner—Carl S. Miller
(74) Attorney, Agent, or Firm—Kubovcik & Kubovcik

(57) ABSTRACT

A piercing needle having a low piercing resistance even if repeatedly caused to pierce is provided. The piercing needle has an undercoat of a silane coupling agent, preferably, an amino group-containing alkoxysilane or an epoxy group-containing alkoxysilane, and an outer surface of a mixture of a (1) reactive silicone such as a reaction product of an amino group-containing alkoxysilane, an epoxy group-containing alkoxysilane and a silicone having silanol groups at both terminal ends, with (2) a non-reactive silicone.

13 Claims, 1 Drawing Sheet

PIERCING NEEDLE

TECHNICAL FIELD OF THE INVENTION

The present invention relates to a piercing needle, and more specifically, to a piercing needle having an improved piercing resistance by means of a surface treatment using silicone compounds.

BACKGROUND OF THE INVENTION

Conventionally, there have been carried out techniques of treating a metal surface with a silicone compound to reduce frictional resistance thereof in various applications. For instance, it is known that a metal cutting blade can be coated with an adhesive coating containing as a main component a copolymer of an aminoalkylsiloxane and a methylsiloxane and maintained under heating or at normal temperature to cure the coating by cross-linkage (Japanese Examined Patent Publication No. Sho46-3627). The piercing resistance of a metal medical needle into a rubber plug or skin is reduced when the needle is coated with the coating substance. However, there arises a problem in that if the needle is repeatedly caused to pierce rubber plugs or skin, the coating substance is peeled off from the needle, thereby increasing the piercing resistance. The reason relates to the fact the coating substance is insufficiently cured. Further, the medical needle must be sterilized, but the piercing resistance of the needle coated with the coating substance may be increased even if it is sterilized by gamma ray irradiation.

The medical needle referred to herein means an injection needle or the like, which is repeatedly used to introduce liquid medicines contained in vials having rubber plugs into injection cylinders and to administer the liquid medicines in the injection cylinders into human bodies. The piercing resistance means the resistance at the time when the needle pierces the rubber plug or the skin. When the resistance is lower, the pain received by a human is less when the needle pierces human skin.

On the other hand, there is known an injection needle, which is obtained by coating a needle with a composition comprising as a main component a reaction product of a polydiorganosiloxane having a silanol group and a reaction product of an amino group-containing silane and an epoxy group-containing silane, and by maintaining the coating under heating or at normal temperature to thereby cure the composition (Japanese Examined Patent Publication No. Sho 61-35780). The composition provides excellent curing properties. However, there arise cases where the piercing resistance is not sufficiently reduced.

Also, there is known an injection needle, which is coated with a coating of a silicone mixture consisting of a silicone containing an amino group in a side chain and/or a terminal end thereof and a polydiorganosiloxane, and is treated on its surface by a curing process including gamma ray irradiation (Japanese Patent Application Laid-open No. Hei 7-178159). The gamma ray irradiation can accelerate the curing of the coating as well as sterilize the injection needle. However, if a sterilization process other than gamma ray irradiation is employed, the coating is not sufficiently cured, and the piercing resistance increases when the needle repeatedly pierces into rubber plugs or the skin.

In view of the above-mentioned problems, the inventors of the present invention discovered a piercing needle, which is coated with a mixture of a silicone obtained by reaction of an amino group-containing alkoxysilane, an epoxy group-containing alkoxysilane and a silicone having silanol groups at both terminal ends thereof, and a non-reactive silicone (U.S. Pat. No. 6,015,398). The piercing needle has a low piercing resistance into rubber plugs or skin, and further has no limitation on its method of sterilization, which is a superior point. However, there has been desired a further improvement so that the piercing resistance becomes better when the piercing needle repeatedly pierces into rubber plugs or the skin.

In consideration of the above-mentioned circumstances, an object of the present invention is to provide a piercing needle having a low piercing resistance even if the needle repeatedly pierces into rubber plug or the skin.

SUMMARY OF THE INVENTION

The inventors of the present invention have made an intensive investigation to solve the above-mentioned problems. As a result, they found that an intended purpose of the present invention can be accomplished by a technique in which a piercing needle is coated with a silane coupling agent, and then coated with a specific silicone mixture. The present invention has been completed based on this finding.

That is, the present invention relates to a piercing needle having an outer surface coated with a compound containing a silane coupling agent, characterized in that the outer surface is further treated with a mixture of a reactive silicone and a non-reactive silicone.

DETAILED DESCRIPTION

Figure 1:
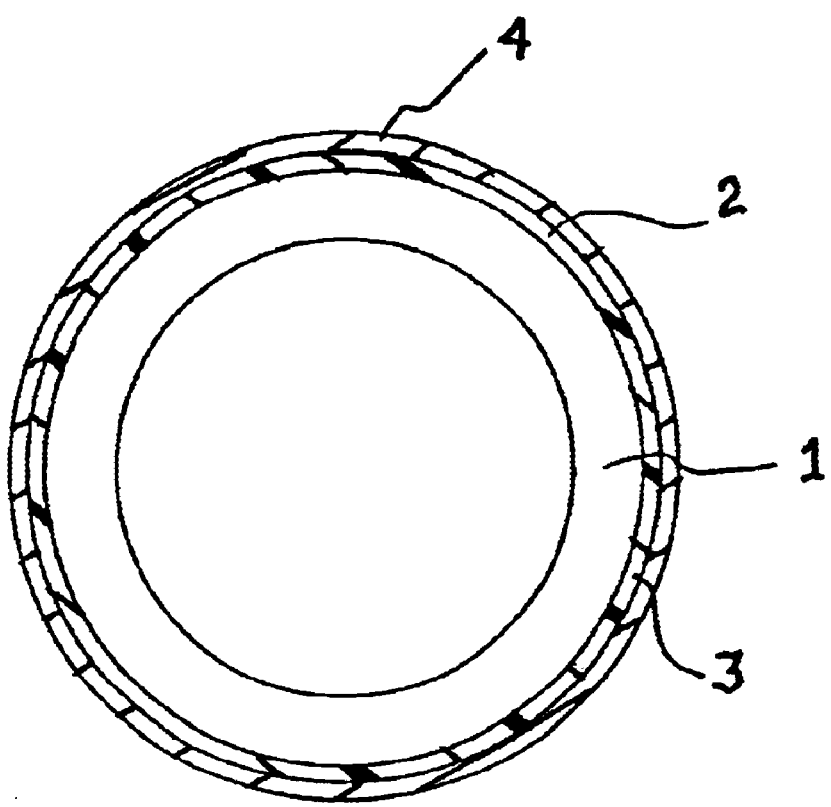
FIG. 1 is a schematic cross-sectional view of the piercing needle of the invention.

Referring to FIG. 1, a cross sectional view of the piercing needle of the invention is shown. The piercing needle 1 has an outer surface 2 coated with an undercoat 3 of a silane coupling agent and an outer surface layer 4 of a mixture of a reactive silicone and a non-reactive silicone.

In the present invention, a piercing needle means a needle such as an injection needle, a wing needle, and a retained needle. Further, the needle is not only limited to such needles but also includes instruments for administering substances such as medicines by piercing an object, or an instrument for collecting blood or the like from a human body.

Any silane coupling agent may be employed in the present invention as far as it is a silane compound having a reactive functional group. For example, there are exemplified one or more compounds selected from the group consisting of a halogen containing silane, an amino group-containing silane, an epoxy group-containing silane, a mercapto group-containing silane, an isocyanate-group containing silane, an azide group-containing silane, a polysulfide group-containing silane, an alkenyl group-containing silane and an alkoxy group-containing silane, and a reaction product thereof. Among these compounds, an amino group-containing alkoxysilane or an epoxy group-containing alkoxysilane, or a reaction product of these compounds is preferred.

The amino group-containing alkoxysilane includes for instance, N-β(aminoethyl)γ-aminopropylmethyldimethoxysilane, N-β(aminoethyl)γ-aminopropyltrimethoxysilane, N-β(aminoethyl)γ-aminopropyltriethoxysilane, γ-aminopropyltrimethoxysilane, γ-aminopropylmethyldiethoxysilane, γ-aminopropyltriethoxysilane and the like.

The epoxy group-containing alkoxysilane includes γ-glycidoxy propyltrimethoxysilane, γ-glycidoxypropylmethyldiethoxysilane, γ-glycidoxypropyltriethoxysilane, β-(3,4-epoxycyclohexyl)ethyltrimethoxysilane and the like.

The silane coupling agent is usually dissolved in an organic solvent which is soluble for the silane coupling agent. Such solvents include hydrocarbons including methanol, ethanol, acetone, ethyl acetate, methyl cellosolve, THF, benzene, toluene, xylene or the like, alcohols, and hydrochlorofluorocarbons (flones) or the like. The concentration of the silane coupling agent is preferably 0.1 to 40% by weight, or more preferably 0.5 to 20% by weight in the solution. If the concentration is less than 0.1% by weight, a needle having low piercing resistance cannot be obtained because the outer surface of the needle cannot be uniformly covered with silane coupling agent. Also, if the concentration is more than 40% by weight, there is a problem in that silane coupling agents in the solution react with each other or the viscosity of the solution increases so that it becomes difficult to coat the solution on a needle.

Into the silane coupling agent, a silicone or the like may be added in an amount which does not affect the properties of the coupling agent. The silicone is preferably a silicone having silanol groups at both terminal ends, and specifically includes dimethylsilicone, methylphenylsilicone, diphenylsilicone or the like.

The amount of the silicone is preferably 50% by weight or less in terms of the above silane coupling agent, preferably 30% by weight or less. If the amount is more than 50% by weight, the ratio of the silane compound having a reactive group is decreased, and the adhesive properties between the silane coupling agent and the needle, and between the silane coupling agent and the silicone mixture used for treating the outer surface thereof, become insufficient so that the mixture of the silane coupling agent and the silicone mixture easily peel off from the needle.

Additionally, an average polymerization degree of a siloxane unit in the silicone is not limited, as long as it is in a range that does not destroy the properties of the silane coupling agent. However, it is preferably 1,000 or less.

The needle used in the present invention includes a needle made of a metal having elasticity such as stainless steel and nickel-titanium, or a needle made of synthetic resin such as PPS resin, ABS resin, PET resin, PP resin, and POM resin. Specifically, an injection needle, a blood collecting needle, a retained needle, a wing needle, a needle for mixing and injecting, a needle for a vial, a needle for suture, and like needles are included herein.

The reactive silicone according to the present invention refers to a silicone having a reactive group, which can react with the above silane coupling agent coated on the needle. There are enumerated, for instance, a silanol group-containing silicone, a methoxy group-containing silicone, a vinyl group-containing silicone, a methylhydrogensilicone, an amino modified silicone, a carboxylic acid modified silicone, a carbinol modified silicone, an epoxy modified silicone, and a mercapto modified silicone.

A reactive silicone which contains an alkoxy group or a silanol group at the terminal end thereof, is specially preferred, since the silicone is reactive with the silane coupling agent and hardly peels off when the needle is repeatedly used for piercing. Further, a silicone, which contains a nitrogen atom in the molecular chain, is preferably used in view of reducing the resistance upon piercing into a rubber plug or needle. Moreover, a silicone containing an epoxy group-containing silane is superior in its curing property. A reactive silicone having such preferable aspects includes a product obtained by the reaction of (a) an amino group-containing alkoxysilane, (b) an epoxy group-containing alkoxysilane, and (c) a silicone having silanol groups at both terminal ends thereof.

Specifically, there are exemplified a reaction product of (a') a polyorganosiloxane having silanol groups at both terminal ends with (b') a reaction product of an organosilane having an amino group at a terminal end with an epoxy group-containing alkoxysilane, and a reaction product of (a") a polyorganosiloxane having amino groups at both terminal ends and having alkoxysilyl groups with (b") an epoxy group-containing alkoxysilane.

One example of synthesizing the above reactive silicone is described below. The synthesis is carried out by the following two steps (1) and (2).

Step (1): A silicone having silanol groups at both terminal ends thereof is reacted with an excess amount of an amino group-containing alkoxysilane. In this reaction, the silanol group in the silicone having silanol groups at both terminal ends thereof is reacted with the alkoxy group of the amino group-containing alkoxysilane so as to form a silicone having amino groups at both terminal ends thereof.

Step (2): And then, the compound obtained in step (1), which is a silicone having amino groups at both terminal ends thereof is reacted with an epoxy group-containing alkoxysilane. In this reaction, mainly, the amino groups in the silicone having amino groups at both terminal ends react with the epoxy groups in the epoxy group-containing alkoxysilane so that a silicone having alkoxy groups at both terminal ends thereof and containing a nitrogen atom in the molecular chain is formed.

The reaction order of synthesizing the reactive silicone is interchangeable. Another example is shown as follows.

Step (1): An amino group-containing alkoxysilane is reacted with an epoxy group-containing alkoxysilane. In this reaction, since the amino groups in the amino group-containing alkoxysilane is mainly reacted with the epoxy groups in the epoxy group-containing alkoxysilane, a silane compound having alkoxy groups at both terminal ends thereof and a nitrogen atom in the molecular chain thereof is obtained, Step (2): And then, an excess amount of the compound obtained in step (1) is reacted with a silicone having silanol groups at both terminal ends thereof. In this reaction, since the silanol groups in the silicone having silanol groups at both terminal ends is reacted with the alkoxy groups at both terminal ends in the compound obtained in step (1), as similar to the previous example, a silicone having alkoxy groups at both terminal ends and containing a nitrogen atom in the molecular chain is obtained.

The process for synthesizing the reactive silicone is not limited to the above two examples, and other known synthesis methods may be employed.

As for the amino group-containing alkoxysilane and the epoxy group-containing alkoxysilane, compounds similar to those used in the silane coupling agent are preferably used.

The silicone having silanol groups at both terminal ends thereof includes polydimethylsiloxane, diphenylsiloxane-diethylsiloxane copolymer, trifluoropropylmethylsiloxane and the like which have silanol groups at both terminal ends.

The non-reactive silicone according to the present invention refers to a silicone which does not have any reactive functional groups that react with the silane coupling agent, and includes, for instance, dimethylsilicone, methylphenylsilicone, alkyl modified silicone, fluorosilicone, polyether modified silicone, fatty acid ester modified silicone and the like.

In the present invention, the reactive silicone is mixed with the non-reactive silicone, and then the surface of the needle coated with the silane coupling agent is treated with the silicone mixture. The mixing ratio of the mixture is preferably 1 to 7 parts by weight of the non-reactive silicone in terms of 10 parts by weight of the reactive silicone.

If the mixing ratio of the non-reactive silicone is less than 1 part by weight, the piercing resistance of the needle into a rubber plug or the skin is not sufficiently decreased. Also, if the mixing ratio is more than 7 parts by weight, there is a possibility for the mixture to peel off when the needle repeatedly pierces a rubber plug or the skin.

The mixture is usually dissolved in an organic solvent such as an aromatic hydrocarbon, straight chain hydrocarbon, aliphatic hydrocarbon, ketone, ether, and chlorofluorocarbon, and is used as a solution. The concentration of the mixture is preferably 1 to 10% by weight, or more preferably 2 to 6% by weight in the solution. If the concentration is less than 1% by weight, it is difficult to provide a uniform coating on the surface of the needle, and a needle having low piercing resistance into a rubber plug or the skin cannot be obtained. Also, if the concentration is more than 10% by weight, it takes a long time to cure the mixture.

It is preferable that the average polymerization degree of the siloxane unit in the reactive silicone is in a range of 10 to 10,000, or preferably, 10 to 1,000. If the average polymerization degree is less than 10, it is difficult for cross-linking of the reactive silicone to occur because of the hindrance of the non-reactive silicone and the curing properties become inferior and increase the piercing resistance of the piercing needle. Also, if the average polymerization degree of the siloxane unit is more than 10,000, there is a tendency that the alkoxy groups at both terminal ends of the reactive silicone do not react with each other, and the cross-linking reaction is unlikely.

Additionally, the average polymerization degree of the siloxane unit in the non-reactive silicone should be less than the average polymerization degree of the siloxane unit of the reactive silicone. If the average polymerization degree of the siloxane unit in the non-reactive silicone is higher than that of the reactive silicone, it is difficult for the cross-linking reaction of the reactive polysiloxane to occur.

In the method for preparing the piercing needle of the present invention, the needle is ordinarily dipped in the solution containing the silane coupling agent for 0.1 to 1 second, and then dried for more than 30 minutes at normal temperature, or for 5 to 120 minutes at a temperature of 60 to 120° C. With this procedure, the silane coupling agent is physically adsorbed on the surface of the needle or a hydroxy group on the surface of the needle is condensed with an alkoxy group in the silane coupling agent to cover the surface of the piercing needle with the silane coupling agent.

Subsequently, the needle is dipped in the solution comprising the mixture of the reactive silicone and the non-reactive silicone for 0.1 to 1 second, and left to stand for more than 24 hours at room temperature or for 5 to 120 minutes at a temperature of 60 to 120° C. By this procedure, an alkoxy group remaining in the silane coupling agent is condensed with an alkoxy group at the terminal of the reactive silicone to adhere the reactive silicone onto the surface of the piercing needle. Further, the mixture is cured by cross-linkage, while the needle is left to stand.

The process for coating the needle with the silane coupling agent and the process for treating the surface of the needle with the mixture may include not only dipping but also brushing, spraying or dropping. Also, in order to accelerate the reaction, an organic acid such as acetic acid may be added to the solution comprising the silane coupling agent or the solution comprising the mixture, or it is preferable to heat the coating for around one hour at a temperature of approximately 100° C.

During the reaction, the non-reactive silicone is not involved in the reaction but exists in the cross-liked reactive silicones and has a role to provide lubricity.

As described above, although the conventional piercing needle has the reactive silicone of the present invention directly adhered on the surface thereof, it is difficult for a condensation reaction with hydroxyl groups to occur on the surface of the piercing needle since the reactive silicone has a large steric hindrance. Therefore, the amount of the reactive silicone adhered on the surface of the piercing needle is small. And there is a concern that the piercing resistance of the piercing needle a rubber plug or the skin is not reduced or the reactive silicone peels off from the surface of the piercing needle to increase the piercing resistance of the needle.

However, the hydroxyl groups on the surface of the piercing needle easily react with the silane coupling agent having little steric hindrance in the needle according to the present invention. Additionally, since one hydroxyl group on the surface of the piercing needle is combined with one molecule of the silane coupling agent having 2 to 6 alkoxy-groups, the number of the adhesion sites in the reactive silicone increases as compared with that of the conventional piercing needle. In other words, the amount of the reactive silicone adhered on the surface of the piercing needle increases. By this procedure, a piercing needle having low piercing resistance can be obtained. Also, even if the piercing needle is repeatedly caused to pierce into a rubber plug or skin, the piercing resistance is low as compared with that of the conventional injection needle.

Even if sterilization is carried out by gamma ray irradiation, there is no fear that the piercing needle according to the present invention will have increased piercing resistance due to excess curing, since the reactive silicone is sufficiently cured. Additionally, the piercing resistance is not increased even when sterilization is carried out by ethylene oxide gas, and therefore the sterilization method is not limited.

Next, a description will be made specifically of an embodiment according to the present invention by referring to examples.

EXAMPLE 1

Coating of the Needle with a Silane Coupling Agent

Two grams of γ-aminopropyltriethoxysilane (KBE-903, manufactured by Shin-etsu Chemicals Co.) was mixed with 1 g of a silicone having silanol groups at both terminal ends thereof (X-22-160AS, manufactured by Shin-etsu Chemicals Co., average polymerization degree: 20) and then dissolved in 90 g of dichloropentafluoropropane (HCFC-141b) to prepare a solution. A 21 G injection needle was dipped in the solution for 0.5 second and subsequently dried for about 60 minutes at normal temperature, and the outer surface of the injection needle was coated therewith.

Treating the Surface of the Needle with a Mixture of a Reactive Silicone and a Non-reactive Silicone 0.6 g of γ-aminopropyltriethoxysilane (KBE-903, manufactured by Shin-etsu Chemicals Co.) was heated and reacted with 0.6 g of γ-glycidoxypropylmethydimethoxysilane (KBM-402, manufactured by Shin-etsu Chemicals Co.) for 3 hours at a temperature of 80° C. The reaction product was mixed with 90 g of a toluene solution comprising polydimethylsiloxane (average polymerization degree, ca 300) having silanol groups at both terminal ends thereof in a concentration of 33% by weight and heated to react for 12 hours at a temperature of 87° C. After completion of the reaction, 8.43 g of the reaction product obtained by the reaction and 4 g of 100 cSt dimethylsilicone (KF96-100, manufactured by Shin-etsu Chemicals Co., average polymerization degree, about 80) were dissolved in dichloropentafluoropropane (HCFC-141b) to prepare 100 ml of a transparent and colorless solution. The pretreated injection needle was dipped in the solution for 0.5 second and subsequently the needle was pulled out and heat-treated for 1 hour at a temperature of 100° C.

The injection needle on which the above heat treatment was carried out was vertically pricked into a natural rubber sheet having a Shore A hardness of 30 and a thickness of 1.5 mm at a cross-head speed of 100 mm/min. The resistance value was measured by a universal tester (AG-500, manufactured by Shimazu Corp.) when the blade of the injection needle was completely penetrated through the natural rubber sheet (first and fifth attempts). Further, the amount of the silicone peeled off from the injection needle and adhered on the sheet surface by the pricking was observed with the eye. The results are shown in Table 1.

EXAMPLE 2

One gram of γ-aminopropyltriethoxysilane (KBE-903, manufactured by Shin-etsu Chemicals Co.) and 1 g of γ-glycidoxypropylmethyldimethoxysilane (KBM-402, manufactured by Shin-etsu Chemicals Co.) were heated and reacted for 3 hours at a temperature of 80° C. The reaction product was dissolved in toluene to prepare 12.5 g of a toluene solution comprising the reaction product in a concentration of 16% by weight. A 21 G injection needle was dipped in the solution for 0.5 second and subsequently dried for about 30 minutes at normal temperature and the silane coupling agent was coated on the outer surface of the injection needle. The needle was treated with the mixture of the reactive silicone and the non-reactive silicone on the surface of the needle in the same manner as in Example 1. The resistance value and the amount of adherence of the silicone were measured. The results are shown in Table 1.

Comparative Example 1

A 21 G injection needle was not coated with a silane coupling agent, but was treated with the mixture of the reactive silicone and the non-reactive silicone on the surface of the needle in the same manner as in Example 1. The resistance value and amount of adherence of the silicone were measured, and the results are shown in Table 1.

TABLE 1

| | Resistance value (g) | | Adherence amount of |
|---|---|---|---|
| | 1st time | 5th time | Silicone |
| Example 1 | 4.5 | 7 | Extremely small |
| Example 2 | 5 | 9 | Extremely small |
| Comparative Example 1 | 9.1 | 9.7 | Small |

As apparent from the results shown in Table 1, the injection needles of the Example 1 and Example 2 coated with the silane coupling agent have a much lower piercing resistance value as compared with the conventional injection needle (Comparative Example 1). Also, the piercing resistance value is lower than that in the first piercing of the conventional injection needle even if piercing was carried out repeatedly. Moreover, the amount of silicone peeled off from the injection needles of Example 1 and Example 2 is less than that of the injection needle of Comparative Example 1.

Effect of the Invention

The piercing needle according to the present invention can lower the resistance upon piercing into a rubber plug or skin compared with that of a conventional injection needle, by employing the technique that the needle is coated with a compound containing the silane coupling agent, and subsequently coated with the mixture of silicones. Also, the piercing resistance is lowered as compared with that of the conventional injection needle even if the piercing into the rubber or the skin is repeatedly carried out, and the amount of the silicone peeled off from the coated surface of the injection needle is extremely small.

What is claimed is:

1. A piercing needle comprising a needle having an undercoat of a silane coupling agent and an outer surface of a mixture of a reactive silicone and a non-reactive silicone, wherein said reactive silicone is a compound containing an alkoxy group in a terminal end and comprising a nitrogen atom in the molecular chain.

2. A piercing needle according to claim 1, wherein said silane coupling agent is one or more compounds selected from the group consisting of a halogen-containing silane, an amino group-containing silane, an epoxy-group containing silane, a mercapto group-containing silane, an isocyanate group-containing silane, an azide group-containing silane, a polysulfide group-containing silane, an alkenyl group-containing silane and an alkoxy group-containing silane, or a reaction product thereof.

3. A piercing needle according to claim 1, wherein said silane coupling agent is one or more compounds selected from the group consisting of an amino group-containing alkoxysilane and an epoxy group-containing alkoxysilane, or a reaction product thereof.

4. A piercing needle according to claim 1, wherein said silane coupling agent is an amino group-containing alkoxysilane selected from the group consisting of N-β (aminoethyl) Υaminopropylmethyldimethoxysilane, N-β (aminoethyl) Y-aminopropyltrimethoxysilane, N-β (aminoethyl)Y-aminopropyltriethoxysilane, Y-aminopropyltrimethoxysilane, Y-aminopropylmethyldiethoxysilane, and Y-aminopropyltriethoxysilane.

5. A piercing needle according to claim 1, wherein said silane coupling agent is an epoxy-containing alkoxysilane selected from the group consisting of γ-glycidoxypropyltrimethoxysilane, γ-glycidoxypropylmethyldiethoxysilane, γ-glycidoxypropyltriethoxysilane and β-(3,4-epoxycyclohexyl) ethyltrimethoxysilane.

6. A piercing needle according to claim 1, wherein said reactive silicone is a compound obtained by the reaction of (a) an amino group-containing alkoxysilane, (b) an epoxy group-containing alkoxysilane and (c) a silicone having silanol groups in both terminal ends thereof.

7. A piercing needle according to claim 1, wherein said reactive silicone is a reaction product of (a') a polyorganosiloxane having silanol groups at both terminal ends with (b') a reaction product of an organosilane having an amino group at a terminal end with an epoxy group-containing alkoxysilane.

8. A piercing needle according to claim 1, wherein said reactive silicone is a reaction product of (a") a polyorganosiloxane having amino groups at both terminal ends and having alkoxysilyl groups with (b") an epoxy group-containing alkoxysilane.

9. A piercing needle according to claim 1, wherein said reactive silicone is a compound obtained by the following steps (1) and (2)
   (1): reacting a silicone having silanol groups at both terminal ends thereof with an amino group-containing alkoxysilane; and
   (2): reacting the compound obtained in step (1) with an epoxy group-containing alkoxysilane.

10. A piercing needle according to claim 1, wherein said reactive silicone is a compound obtained by the following steps (1) and (2):
    (1): reacting an epoxy group-containing alkoxysilane with an amino group-containing alkoxysilane; and
    (2): reacting the compound obtained in the step (1) with a silicone having silanol groups at both terminal ends thereof.

11. A piercing needle according to claim 1, wherein said non-reactive silicone is one or more compounds selected from the group consisting of dimethylsilicone, methylphenylsilicone, alkyl modified silicone, fluorosilicone, polyether modified silicone and fatty acid ester modified silicone.

12. A piercing needle according to claim 1, wherein a mixing ratio of said mixture is 1 to 7 parts by weight of the non-reactive silicone based on 10 parts by weight of the reactive silicone.

13. A piercing needle according to claim 1, wherein an average polymerization degree of siloxane unit in said reactive silicone is 10 to 10,000, and an average polymerization degree of siloxane unit in said non-reactive silicone is no more than the average polymerization degree of the siloxane parts of the reactive silicone.

* * * * *